United States Patent
Majercak

(10) Patent No.: US 8,690,937 B2
(45) Date of Patent: Apr. 8, 2014

(54) STENT GRAFT DEVICE

(71) Applicant: David C. Majercak, Stewartsville, NJ (US)

(72) Inventor: David C. Majercak, Stewartsville, NJ (US)

(73) Assignee: Cordis Corporation

( * ) Notice: Subject to any disclaimer, the term of this patent is extended or adjusted under 35 U.S.C. 154(b) by 0 days.

(21) Appl. No.: 13/629,054

(22) Filed: Sep. 27, 2012

(65) Prior Publication Data

US 2013/0023978 A1    Jan. 24, 2013

Related U.S. Application Data

(62) Division of application No. 11/376,641, filed on Mar. 15, 2006, now Pat. No. 8,357,194.

(51) Int. Cl.
*A61F 2/06* (2013.01)

(52) U.S. Cl.
USPC .......................................................... 623/1.13

(58) Field of Classification Search
USPC ................ 606/108, 192, 194; 623/1.11–1.16, 623/1.18–1.2, 1.35, 1.36
See application file for complete search history.

(56) References Cited

U.S. PATENT DOCUMENTS

| | | | |
|---|---|---|---|
| 4,787,899 A | 11/1988 | Lazarus | |
| 5,104,399 A | 4/1992 | Lazarus | |
| 5,219,355 A | 6/1993 | Parodi et al. | |
| 5,275,622 A | 1/1994 | Lazarus et al. | |
| 5,316,023 A | 5/1994 | Palmaz et al. | |
| 5,665,115 A | 9/1997 | Cragg | |
| 5,780,807 A | 7/1998 | Saunders | |
| 5,843,158 A | 12/1998 | Lenker et al. | |
| 6,221,102 B1 | 4/2001 | Baker et al. | |
| 6,231,598 B1 | 5/2001 | Berry et al. | |
| 6,248,116 B1 | 6/2001 | Chevillon et al. | |
| 6,556,115 B1 | 4/2003 | Fahley et al. | |
| 6,929,658 B1 | 8/2005 | Freidberg et al. | |
| 7,238,198 B2 | 7/2007 | Hartley et al. | |
| 2002/0007212 A1 | 1/2002 | Brown et al. | |
| 2002/0123792 A1 | 9/2002 | Burgermeister | |
| 2003/0208260 A1 | 11/2003 | Lau et al. | |
| 2004/0073289 A1 | 4/2004 | Hartley | |
| 2004/0106978 A1 | 6/2004 | Greenberg et al. | |
| 2004/0117004 A1 | 6/2004 | Osborne et al. | |
| 2005/0137677 A1 | 6/2005 | Rush | |
| 2005/0159803 A1 | 7/2005 | Lad et al. | |
| 2006/0030930 A1 | 2/2006 | Burgermeister et al. | |
| 2006/0184227 A1 | 8/2006 | Rust | |
| 2007/0055347 A1 | 3/2007 | Arbefeuille | |

FOREIGN PATENT DOCUMENTS

| | | |
|---|---|---|
| EP | 1 029 517 A2 | 8/2000 |
| EP | 1 759 669 A1 | 3/2007 |
| FR | 2 773 057 A | 7/1999 |
| JP | 2001517483 A | 10/2001 |
| JP | 2005199054 A | 7/2005 |

*Primary Examiner* — Thomas McEvoy
*Assistant Examiner* — Jocelin Tanner

(57) ABSTRACT

A stent graft device for implanting in a body lumen, comprising a stent with non-staggered or staggered apexes, said stent comprising a plurality of stent sections, bendable connecting members forming said non-staggered or staggered apexes and connecting each of said stent sections to other stent sections to form a zigzag pattern, wherein said stent is staggerdly sutured to a graft by a plurality of suture knots, and wherein said suture knots and staggered apexes are staggered when said stent sections are crimped, and methods of use thereof.

9 Claims, 3 Drawing Sheets

STENT GRAFT DEVICE

CROSS-REFERENCE TO RELATED APPLICATIONS

This application is a divisional of U.S. application Ser. No. 11/376,641 filed on Mar. 15, 2006, which is hereby incorporated by reference in its entirety.

BACKGROUND OF THE INVENTION

The invention relates generally to endoprostheses and, more specifically, to a stent graft device for delivery to an area of a body lumen that has been weakened by damage or disease, such as an aneurysm of the abdominal aorta. Several areas of the body are particularly suitable for receiving an endoprosthesis, commonly referred to as an intraluminal stent to hold open and insure the patency of a body lumen. Two such areas include the coronary arteries and the aorta, especially in the area where an aneurysm has developed.

An abdominal aortic aneurysm ("AAA") is an abnormal dilation of the arterial wall of the aorta in the region of the aorta that passes through the abdominal cavity. The condition most commonly results from atherosclerotic disease. Frequently, abdominal aortic aneurysms are dissecting aneurysms, that is aneurysms that are formed when there is a tear or fissure in the arterial lining or wall through which blood is forced and eventually clots, forming a thrombosis which swells and weakens the vessel. Abdominal aortic aneurysms do not cause pain, but can be detected in a thorough physical examination. If the aneurysm is not detected and treated, it is likely to rupture and cause massive hemorrhaging fatal to the patient.

AAAs have been traditionally treated by some form of arterial reconstructive surgery which commonly is referred to as a "triple-A" procedure. One such method is by-pass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished. The graft commonly is fabricated of a biocompatible material that is compliant and thin-walled. Nylons and synthetic fibers such as those manufactured under the trademarks DACRON or TEFLON have been found to be suitable for the construction of the graft. Studies have shown that the mortality rate associated with this surgical procedure is favorable (less than 5%) when it is performed prior to rupture of an aneurysm. However, patients having an AAA typically are over 65 years of age, and often have other chronic illnesses which increase the risk of perioperative or post-operative complications. Those patients thus are not ideal candidates for this type of major surgery. Further, it has been pointed out that this procedure is not often successfully resorted to after an aneurysm has ruptured (the mortality rate increases to over 65%) because of the extensiveness of the surgery and the time required to prepare a patient for it.

Because of the aforementioned disadvantages to conventional surgical methods, another procedure was developed as an alternative to conventional, major surgery. This method also involves emplacement of a graft at the site of the aneurysm; however, the graft is deployed there by being routed through the vascular system carried by a catheter, wire or other device suitable for negotiating the vasculature.

More recently, grafts have been used in combination with stents, wherein the apexes of the stents are aligned circumferentially when the stent is crimped which may increase the overall delivery profile. There is an ongoing need for lower profile stents-grafts for treating AAA in order to better treat patients less invasively.

SUMMARY OF THE INVENTION

One aspect of the invention relates to a stent graft device for implanting in a body lumen, comprising a stent with non-staggered apexes, said stent comprising a plurality of stent sections, bendable connecting members forming said non-staggered apexes and connecting each of said stent sections to other stent sections to form a zigzag pattern, wherein said stent is staggerdly sutured to a graft by a plurality of suture knots, and wherein said suture knots are staggered when said stent sections are crimped.

Another aspect of the invention relates to a stent graft device for implanting in a body lumen, comprising a stent with staggered apexes, said stent comprising a plurality of stent sections, bendable connecting members forming said staggered apexes and connecting each of said stent sections to other stent sections to form a zigzag pattern, wherein said stent is staggerdly sutured to a graft by a plurality of suture knots, and wherein said apexes and said suture knots are staggered when said stent sections are crimped.

In other embodiments, some of the staggered apexes of the stent graft devices described above are projected and contact and penetrate the body lumen.

Preferably, the stents have staggered apexes and the staggered apexes are sufficiently close to the suture knots to substantially prevent micromotion of the apexes.

In other embodiments, the stent sections are formed from a single piece of tubing.

In other embodiments, the stent sections are formed from a flat sheet of material.

Another aspect of the invention relates to a method for implanting the stent graft devices described above comprising:

a) providing a delivery catheter;
b) mounting the stent graft device onto the catheter;
c) delivering the stent graft device percutaneously through the patient's vasculature to a specific location;
d) deploying the stent graft device into the body lumen; and
e) withdrawing the catheter from the patient leaving the stent graft device deployed in the body lumen.

The above method can employ the stent with staggered apexes or non-staggered apexes in the stent graft device.

In another embodiment, the method of implanting the stent graft device further comprises positioning the stent graft device at the aneurysm, and affixing the stent graft device to the aortic wall where the aneurysm is. In this embodiment, it is preferred that the stent graft device is used for repairing abdominal aortic aneurysm.

Other features and advantages of the present invention will become more apparent from the following detailed description of the invention, and taken in conjunction with the accompanying exemplary drawings.

DETAILED DESCRIPTION OF THE INVENTION

Figure 1:
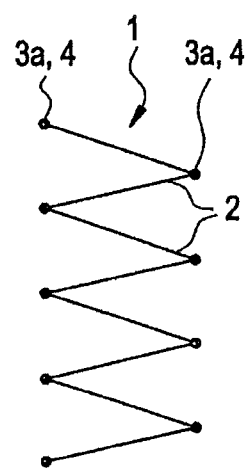
FIG. 1. depicts a typical stent graft device using a stent (1) with non-staggered apexes (3a), wherein the non-staggered apexes (3a) and suture knots (4) are aligned to create a localized profile increase.
Figure 2:
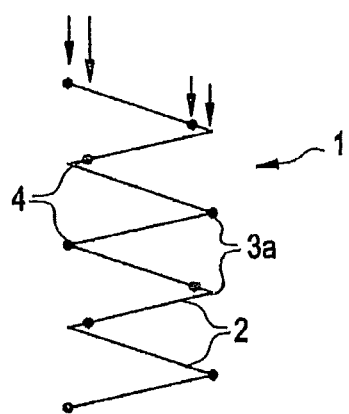
FIG. 2. depicts a stent graft device of the present invention using a stent (1) with non-staggered apexes (3a), wherein the stent (1) is staggerdly sutured by a plurality of suture knots (4) which are staggered when crimped to reduce the profile.

The invention relates to a stent graft device for implanting in a body lumen. FIG. 2 shows a stent (1) with non-staggered apexes (3a), wherein the stent (1) comprises a plurality of stent sections (2), bendable connecting members forming the non-staggered apexes (3a) and connecting each of the stent sections (2) to other stent sections (2) to form a zigzag pattern, wherein the stent (1) is staggerdly sutured to a graft by a plurality of suture knots (4), and wherein the suture knots (4) are staggered when the stent sections (2) are crimped.

Figure 3:
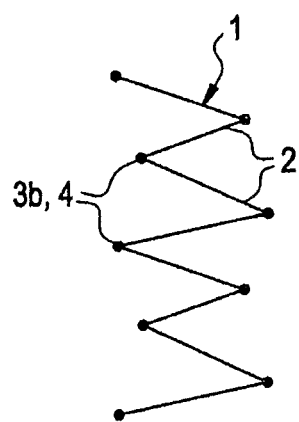
FIG. 3. depicts a stent graft device of the present invention using a stent (1) with staggered apexes (3b), wherein the stent (1) is staggerdly sutured by a plurality of suture knots (4) which are staggered when crimped to reduce the profile.

Another aspect of the invention relates to a stent graft device for implanting in a body lumen, as depicted in FIG. 3, comprising a stent (1) with staggered apexes (3b), wherein the stent (1) comprises a plurality of stent sections (2), bendable connecting members forming the staggered apexes (3b), and connecting each of the stent sections (2) to other stent sections (2) to form a zigzag pattern, wherein the stent (1) is staggerdly sutured to a graft by a plurality of suture knots (4), and wherein the staggered apexes (3b) and suture knots (4) are staggered when the stent sections (2) are crimped.

It is contemplated in this invention that the stent graft device can comprise one or more stents (1) sutured to a graft.

When the stent (1) used in the stent graft device has non-staggered apexes (3b), the non-staggered apexes (3a) are not as close to the sutured knots (4) as when the stent (1) which has staggered apexes (3b). In a preferred embodiment, the stent (1) has staggered apexes (3b) and the staggered apexes (3b) are sufficiently close to the suture knots (4) to substantially prevent micromotion of the staggered apexes (3b). Apexes and terminated point-like knots create local bulk and when aligned circumferentially create large and localized bulk, therefore, staggering these areas reduce profile.

Grafting systems, which are systems that include a graft and a stent, that are known in the art can be used in the present invention, and these grafting systems are typically made of biocompatible material and can include an attachment system for anchoring the graft to a body lumen. The stent can be a tubular device which is fitted inside and is generally coaxial with the graft. The stent can also extend out of the graft. The attachment system can have a lattice-like or open weave structure, which provides it with flexibility and which promotes rapid endothelial tissue growth through the structure once the graft has been deployed. It can be provided with additional hook-like elements for penetration of the intimal walls for attachment of the graft to the aorta, or those hook-like elements can be provided on the graft itself. Graft systems described in U.S. Pat. No. 4,787,899 (Lazarus); U.S. Pat. No. 5,104,399 (Lazarus); U.S. Pat. No. 5,219,355 (Parodi et al.); and U.S. Pat. No. 5,275,622 (Lazarus), which are incorporated herein by reference, can be used in the present invention. Furthermore, it should be understood to one skilled in the art that any point-like attachment mechanisms such as staples, clamps, etc., can be used.

The actual function of delivering the graft can be accomplished by inflating a balloon of a catheter by introducing pressurized fluid into a lumen of the catheter from a source external to the patient. Inflation of the balloon applies a force to the graft and any attachment system supplied therein which extends radially and presses the graft and attachment system into the vessel wall just above and just below the aneurysm.

In another embodiment, the stent-graft device can be delivered intraluminally by being mounted on the balloon portion of a delivery catheter and delivered intraluminally in a portion of a body lumen. Once the stent graft device is positioned at the site where it is to be implanted, the balloon portion of the catheter can be expanded by known means to expand the stent outwardly into contact with the body lumen. The balloon portion of a delivery catheter can be substituted for by any expansion member capable of receiving the stent graft device and expanding or urging the stent graft device outwardly into contact with the body lumen. Other non-limiting means that are available to urge outwardly and expand the stent graft device include mechanical, hydraulic, pneumatic, and phase transition using memory-shaped alloys or superelastic alloys.

For example, the stent graft device can be mounted on a balloon and delivered intraluminally by an over-the-wire catheter. Guidewire can be used to navigate the patient's vasculature and assist in positioning the catheter and balloon carrying the stent graft device.

The graft and its deployment system can be introduced into the blood stream percutaneously with a femoral approach and the entire procedure can be performed using local or general anesthesia.

Once the stent graft device has been positioned at the aneurysm, it can be disengaged from the delivery system and can be affixed to the aortic wall where the aneurysm is. For this purpose, grafting systems can include fixation means such as staples or hooks which can be manipulated and driven into the intima of the vessel via some mechanical feature of the system, or by some physical process, such as expansion of the graft through application of pressure. To avoid premature detachment of the stent graft device and to prevent the attachment elements from damaging the vessels or halting the forward movement of the system while the stent graft device is being routed to the treatment site, the systems can be provided with a feature such as a capsule or a sheath that protects and contains the stent graft device until such time as deployment is desired.

Once the stent graft device is in place, it can be positioned in the vessel spanning the site of the aneurysm such that the walls of the stent graft device are generally parallel to the walls of the affected area of the aorta. The aneurysm thus is excluded from the circulatory system by the stent graft device. If the aneurysm is a dissecting type and a thrombosis exists between the walls of the aorta, the now-excluded aneurysm can beneficially provide structural support for the stent graft device.

Other devices which can be used to attach the graft to the aortic wall for AAA repair can include intravascular stents of the type found in U.S. Pat. No. 5,316,023.

In another embodiment, the stent sections (2) which are used in the stent graft device, for the treatment and repair of aneurysms, is composed of a biocompatible material and is simultaneously flexible enough to comply with the catheter or other element used to route the stent graft device through the vascular path to the site of the aneurysm and strong enough radially to maintain the opening in the stent graft device once delivered. In another embodiment, the stent graft device can affix itself to the aortic walls. For instance, the stent (1) can have hooks or jagged ends to enable the stent to affix itself to the aortic wall.

It is also contemplated that each of the embodiments can be used in the stent graft device to repair other body lumens such as the coronary arteries. Thus, for example, the stent graft device of the present invention can be implanted in a coronary artery after a PTCA procedure in order to repair a damaged or diseased portion of the artery. The stent (1) will be deployed and implanted similar to that described above, with the exception that stent graft device may be correspondingly smaller in the coronary arteries than in the aorta.

The stent graft device can be used in the invention and can be made of any known tubular graft or bifurcated graft. Preferably, the stent graft device is used for repairing an aortic aneurysm, coronary arteries, and other vessels, however, other body lumens are equally suited to receive the stent graft device of the present invention.

In keeping with the invention, FIGS. 2 and 3 depicts stent sections (2) which are connected by a plurality of bendable connecting members forming non-staggered apexes (3*a*) as shown in FIG. 2) and staggered apexes (3*b*) as shown in FIG. 3). The stent sections (2) can be formed from a flat sheet of material. Alternatively, the stent sections (2) can be formed from a piece of tubing using known chemical etching or laser cutting techniques.

It is advantageous for the stent graft device to have suture knots (4) that are staggerdly stitched to the stent graft device to lower the profile. In a particularly preferred embodiment, the stent (1) in the stent graft device has staggered apexes (3*b*) and the staggered apexes (3*b*) are sufficiently close to the suture knots (4) to substantially prevent micromotion of the staggered apexes (3*b*). The staggered apexes (3*b*) enables the stent graft device to have a lower profile so that the contents of the stent graft device are more evenly distributed throughout and are easier to deliver.

It is preferred to position the stent graft device so that it spans the aneurysm and diverts blood flow from the aorta through the stent graft device, so that no blood flow leaks around the stent graft device and into the aneurysm. Preferably the cranial end of the stent graft device is positioned in the aortic wall where there is healthy tissue, and not where the aneurysm has weakened the vessel wall.

Although a particular form of catheter has been described to route the stent graft device to the aneurysm, it will be apparent to those skilled in the art in treating aneurysms and similar conditions, that catheters having various configurations could be used successfully to perform the same functions. For example, well-known fixed wire and rapid exchange wire systems also can be used in the delivery system described above.

The stent sections (2) can be made of stainless steel by itself, or in combination with other materials. Other materials, in addition to stainless steel, for the stent sections (2) are contemplated, which include tungsten, platinum, gold, titanium, elgiloy, heat activatable metal such as NITINOL, polymer materials, or combinations thereof. The thickness of the metal can be in the range of about 0.25 to about 0.50 millimeters in thickness. Preferably, the stent sections (2) are made of NITINOL.

The stent sections (2) can be formed, for example, from a flat sheet of material or from a single sheet of stainless steel tubing by chemically etching, laser cutting, or by using electronic discharge machining. For example, the stent sections (2) can be made according to the description of U.S. Pat. No. 5,780,807, which is incorporated herein by reference.

It is also contemplated that the bendable connecting members forming the staggered apexes (3*b*) or non-staggered apexes (3*a*) include an area along the connecting member made of a material that is thinner or necked-down relative to the rest of the connecting member. The bendable connecting member can also be formed by a metal different from the metal forming the rest of the stent (1) or by selectively treating an area of the native material. For example, the stent sections (2) can be formed from stainless steel, while the bendable connecting member can be formed from any material having a lower modulus of elasticity which will bend more easily than the stainless steel.

While the invention has been illustrated and described herein in terms of its use as a stent-graft device for use in the aorta to repair an aortic aneurysm, it will be apparent to those skilled in the art that the stent graft device can be used in other instances in other vessels of the body.

Other modifications and improvements can be made without departing from the scope of the invention. For example, the various drawing figures depict several configurations of the stent (1) and various sizes, each of which can be modified to suit a particular application without departing from the spirit and scope of the invention.

What is claimed is:

1. A method of implanting a stent graft device comprising:
    a) providing a delivery catheter;
    b) mounting said stent graft device onto said catheter, said stent graft device comprising a tubular stent having a first unexpanded diameter when mounted on the delivery catheter and a second expanded diameter once deployed and defining a longitudinal direction and a circumferential direction, the stent comprising a plurality of individual stent segments each having a zigzag shaped pattern formed into a tubular shape with a first open end and a second open end, wherein the first open end has a row of first apexes coming to a point and the second open end has a row of second apexes coming to a point, the apexes in the row of first apexes being aligned in the circumferential direction with one another and the apexes in the row of second apexes being aligned in the circumferential direction with one another but not with the apexes in the row of first apexes; and graft material affixed to the stent to create a fluid carrying conduit, the graft material being affixed to the stent by a plurality of sutures that are knotted, the suture knots being stitched to the graft material sufficiently close to the apexes in a staggered pattern relative to the circumferential direction such that each suture knot has an associated apex by virtue of its proximity to the sufficiently close apex, whereas the suture knots associated with circumferentially adjacent apexes in the same row of apexes are not circumferentially aligned, and wherein the circumferentially adjacent suture knots associated with the apexes in the same row do not touch one another when the stent segment is at its first unexpanded diameter;
    c) delivering said stent graft device percutaneously through a patient's vasculature to a specific location in a body lumen;
    d) deploying said stent graft device into the body lumen; and
    e) withdrawing said catheter from said patient leaving said stent graft device deployed in the body lumen.

2. The method of implanting a stent graft device according to claim 1, further comprising positioning said stent graft device at an aneurysm in the vasculature, and affixing said stent graft device to a lumen wall adjacent the aneurysm is.

3. The method of implanting a stent graft device according to claim 2, further comprising affixing said stent graft device in an abdominal aorta proximal and distal to an abdominal aortic aneurysm.

4. The method of implanting a stent graft device according to claim 1 further comprising reducing the profile of said stent graft by further crimping said stent graft device, causing said apexes and said suture knots to become more staggered.

5. The stent graft device according to claim 1, wherein said apexes are sufficiently close to said sutured knots to substantially prevent micromotion of said apexes.

6. The stent graft device according to claim 1, wherein said stent sections are comprised of stainless steel, tungsten, platinum, gold, titanium, elgiloy, heat activatable NITINOL, polymer materials, or combinations thereof.

7. The stent graft device according to claim 6, wherein said stent sections are comprised of NITINOL.

8. The stent graft device according to claim 1, wherein said stent sections are formed from a single piece of tubing.

9. The stent graft device according to claim 1, wherein said stent sections are formed from a flat sheet of material.

* * * * *